United States Patent
Kodama et al.

(10) Patent No.: US 10,175,247 B2
(45) Date of Patent: Jan. 8, 2019

(54) PHYSICAL CHANGE EVALUATION DEVICE, METHOD, AND RECORDING MEDIUM STORED WITH PROGRAM

(71) Applicant: TANITA CORPORATION, Tokyo (JP)

(72) Inventors: Miyuki Kodama, Tokyo (JP); Ayumi Sano, Tokyo (JP); Yasuhiro Kasahara, Tokyo (JP); Naotaka Minagawa, Tokyo (JP); Moe Watabe, Tokyo (JP)

(73) Assignee: Tanita Corporation, Tokyo (JP)

( * ) Notice: Subject to any disclaimer, the term of this patent is extended or adjusted under 35 U.S.C. 154(b) by 432 days.

(21) Appl. No.: 14/619,175

(22) Filed: Feb. 11, 2015

(65) Prior Publication Data

US 2015/0226747 A1 Aug. 13, 2015

(30) Foreign Application Priority Data

Feb. 13, 2014 (JP) .................................. 2014-025640

(51) Int. Cl.
*A61B 5/08* (2006.01)
*G01N 33/64* (2006.01)
*G06F 19/00* (2018.01)

(52) U.S. Cl.
CPC ......... *G01N 33/64* (2013.01); *G06F 19/3475* (2013.01)

(58) Field of Classification Search
CPC combination set(s) only.
See application file for complete search history.

(56) References Cited

U.S. PATENT DOCUMENTS

| 2003/0208133 | A1* | 11/2003 | Mault | A61B 5/0002 600/532 |
| 2003/0223905 | A1* | 12/2003 | Moerman | A61B 5/411 422/400 |
| 2003/0226695 | A1* | 12/2003 | Mault | A61B 5/0002 177/25.16 |
| 2009/0054799 | A1* | 2/2009 | Vrtis | G01N 33/497 600/532 |

FOREIGN PATENT DOCUMENTS

| JP | 2001-349888 A | 12/2001 |
| JP | 2011-519592 A | 7/2011 |
| WO | 2009/131664 A2 | 10/2009 |
| WO | 2013/038959 A1 | 3/2013 |

OTHER PUBLICATIONS

Office Action issued in Chinese Patent Application No. 201510067849.5 dated Feb. 17, 2017.
Office Action issued in corresponding Japanese Patent Application No. 2017-174041 dated Aug. 21, 2018.

* cited by examiner

*Primary Examiner* — Mitchell E Alter
(74) *Attorney, Agent, or Firm* — Morgan, Lewis & Bockius LLP

(57) ABSTRACT

The invention provides a physical change evaluation device, method, and program capable of easily evaluating physical change from the past to the present, and from the present into the future.

A physical change evaluation device 10 acquires a ketone concentration measurement measuring ketone excreted from a user, acquires physical data relating to the body of the user, evaluates physical change in the user based on the acquired ketone concentration measurement and the physical data, and outputs an evaluation result.

6 Claims, 10 Drawing Sheets

| ACETONE CONCENTRATION | FAT METABOLISM |
|---|---|
| * TO * ppb | LOW |
| * TO * ppb | STANDARD |
| * TO * ppb | HIGH |
| * TO * ppb | TOO HIGH |

FIG.8 70

| EVALUATION NO. | BODY FAT CHANGE DIRECTION | ADVICE INFORMATION |
|---|---|---|
| 1, 2 | Body fat UP | Your body fat is not decreasing because you're eating too much or not exercising enough. Your fat burn is down too. If you carry on like this you might find your body fat increasing! |
| 1, 2 | Body fat DOWN | Muscle mass is UP! Your current progress is OK, but your fat burn is going down. You're at high risk of putting on weight. Be careful! |
| 3 | Body fat UP | Puffiness improving, water retention decreasing. Your fat burn is down. If you carry on like this you could put on weight. Be careful! |
| 3 | Body fat DOWN | Your body fat is falling nicely and you've been reducing it at a good rate so far, but your fat burn is on the way down. Be careful from now on! |
| 4 | Body fat UP | You're at risk of dehydration! Take fluids immediately! Your fat is not burning up. You're not skipping meals, are you? I'm worried about your health. |
| 4 | Body fat DOWN | Don't you think you're losing weight excessively? Your fat burn is currently on the way down. I'm worried that you could be heading toward a sudden rebound. |
| 5, 6 | Body fat UP | Your body fat is not decreasing because you're eating too much or not exercising enough. Your fat burn isn't increasing either, so it doesn't look like you'll lose any more weight. |
| 5, 6 | Body fat DOWN | Fat is down and muscle mass is UP! Your progress is OK. Your fat burn isn't going up so it you'll probably stay about the same. |
| 7 | Body fat UP | Puffiness improving, water retention decreasing. Have a think about what you are eating. Your fat burn isn't going up so it looks like you'll be able to maintain this weight. |
| 7 | Body fat DOWN | Your body fat is falling nicely and you're reducing it at a good rate. Your fat burn is standard so you'll probably be able to maintain this weight. |
| 8 | Body fat UP | You're at risk of dehydration! Take fluids immediately! Your fat burn is standard so it doesn't look like you'll lose any more weight. |
| 8 | Body fat DOWN | Don't you think you're losing weight excessively? Your fat burn is currently standard so it doesn't look like you'll lose any more fat, but be careful! |
| 9, 10 | Body fat UP | Your body fat doesn't seem to have decreased yet, but you've just started burning fat steadily. You should be losing weight soon. |
| 9, 10 | Body fat DOWN | Your fat is down and your muscle mass is going UP! Your fat burn is still on the way up too! You should lose weight nicely from now on. |
| 11 | Body fat UP | Puffiness improving, water retention decreasing. Your fat burn is on the way up and it looks like you'll be losing fat soon. |
| 11 | Body fat DOWN | Your body fat is falling nicely and you're reducing it at a good rate. Your fat burn is still on the way up too! You should keep losing fat from now on. |
| 12 | Body fat UP | You're at risk of dehydration! Your fat burn is on the way up, so make sure you drink plenty of fluids to aid good metabolism. |
| 12 | Body fat DOWN | Don't you think you're losing weight excessively? Your fat burn is on the way up too. Take care not to overdo it. |
| 13, 14 | Body fat UP | Your body fat isn't decreasing, but fat burn has started to shoot up. Are you sure you're not limiting your dietary intake too much? |
| 13, 14 | Body fat DOWN | Your fat is down and your muscle mass is going UP! Your fat burn is currently shooting up. Take care not to overdo it. |
| 15 | Body fat UP | Puffiness improving, water retention decreasing. Your fat burn is way up. You're not excessively limiting your dietary intake by skipping meals, are you? |
| 15 | Body fat DOWN | Your body fat is falling nicely and you're reducing it at a good rate, but your fat burn has shot up too far. Take care not to lose weight too fast. |
| 16 | Body fat UP | You're at risk of dehydration, and your fat burn has shot up too far too. You're not excessively limiting your dietary intake by skipping meals, are you? |
| 16 | Body fat DOWN | Don't you think you're losing weight excessively? Your fat burn has also shot up too far. Take care not to overdo it. |

FIG.9    80

| EVALUATION NO. | ADVICE INFORMATION |
|---|---|
| 1 | You won't lose weight.  Your fat burn is going down, so you're at high risk of weight increasing if you carry on like this! |
| 2 | Going steady.  However your fat burn is going down so you may start putting on weight. |
| 3 | You're losing weight nicely.  However your fat burn is going down so you may start putting on weight. |
| 4 | Be careful of losing weight too fast.  Your fat burn is on the way down too, and you're at risk of heading for a major rebound. |
| 5 | You won't lose weight.  Your fat burn isn't increasing either, so you'll have to try harder if you want to lose weight. |
| 6 | Going steady.  Your fat burn isn't increasing, so it looks like you'll be able to maintain this weight. |
| 7 | You're losing weight nicely.  Your fat burn isn't increasing, so it looks like you'll be able to maintain this weight. |
| 8 | Be careful of losing weight too fast.  Your fat burn is under control.  It It looks like you'll be able to maintain this weight and not lose further weight. |
| 9 | Your body weight is increasing, but you're burning fat steadily right now. You should be losing weight soon. |
| 10 | Your body weight is still the same so far, but you're burning fat steadily right now.  You should be losing weight soon. |
| 11 | You're losing weight nicely.  You're burning fat steadily right now. You should lose weight nicely from now on. |
| 12 | Be careful of losing weight too fast.  You're burning fat steadily right now. Take care not to make yourself ill by losing weight too fast. |
| 13 | Your body weight is increasing, but your fat burn has started to shoot up. You're not excessively limiting your dietary intake, are you? |
| 14 | Your body weight is still the same so far, but your fat burn has started to shoot up.  You're not excessively limiting your dietary intake, are you? |
| 15 | You're losing weight nicely.  Your fat burn is shooting up right now.  Take Take care not to overdo it. |
| 16 | Be careful of losing weight too fast.  Your fat burn is shooting up too. Are you sure you're not overdoing it?  Look after your health. |

PHYSICAL CHANGE EVALUATION DEVICE, METHOD, AND RECORDING MEDIUM STORED WITH PROGRAM

CROSS-REFERENCE TO RELATED APPLICATION

This application is based on and claims the benefit of priority of the prior Japanese Patent Application No. 2014-025640, filed on Feb. 13, 2014, the entire contents of which are incorporated herein by reference.

BACKGROUND

Technical Field

The present invention relates to a physical change evaluation device, method, and program.

Related Art

In order to go on a diet healthily, it is necessary to reduce body fat in an appropriate manner. It is therefore necessary to ascertain a body fat burn state, and exercise and eat appropriately.

It is known that a body fat burn state can be ascertained through measuring acetone concentration in the breath. For example, Patent Document 1 describes a diet support system that meters the breath acetone concentration, and determines appropriate timings for dietary intake and appropriate timings for taking exercise according to an analysis result of the metered acetone concentration.

Changes in body weight and body fat appear as the accumulated result of long-term past living practices. Effort in dieting or exercising produces virtually no change at the level of a few hours, making it difficult to maintain motivation when dieting. However, fat metabolism evaluation using ketone concentration in biological gasses or urine, for example, measures results of effort over a few hours, and are therefore highly effective as short term indices.

Patent Document 1: International Publication No. 2013/038959

However, conventional fat metabolism evaluation using ketone concentration in biological gasses or urine cannot be evaluated instantly on the spot, and is therefore not something capable of evaluating physical change from the past to the present, or evaluating ongoing physical change from the present into the future.

SUMMARY

An object of the present invention is to provide a physical change evaluation device, method, and program capable of easily evaluating physical change from the past to the present, and from the present into the future.

In order to address the above issues, a physical change evaluation device of a first aspect of the invention includes a ketone concentration acquisition section that acquires a ketone concentration measurement measuring ketone excreted from a user, a physical data acquisition section that acquires physical data relating to the body of the user, an evaluation section that evaluates physical change in the user based on the ketone concentration measurement acquired by the ketone concentration acquisition section and the physical data, and an output section that outputs an evaluation result by the evaluation section.

As in a second aspect of the invention, configuration may be made such that the physical data acquisition section acquires as the physical data at least one out of body weight data of the user or body composition data of the user, and the evaluation section evaluates physical change in the user based on the ketone concentration measurement and at least one piece of physical data out of the body weight data of the user or the body composition data of the user.

As in a third aspect of the invention, configuration may be made such that the physical data acquisition section acquires the physical data that is current and past, and the evaluation section evaluates physical change in the user based on the ketone concentration measurement and a comparison result between the current physical data and the past physical data.

As in a fourth aspect of the invention, configuration may be made such that the output section outputs advice information corresponding to the evaluation result.

As in a fifth aspect of the invention, configuration may be made further including a measurement section that measures ketone excreted from the user.

As in sixth aspect of the invention, configuration may be made further including a metering section that meters physical data relating to the body of the user.

As in seventh aspect of the invention, the ketone excreted from the user may be acetone contained in breath exhaled from the user.

A physical change evaluation method of an eighth aspect of the invention includes acquiring a ketone concentration measurement measuring ketone excreted from a user, acquiring physical data relating to the body of the user, evaluating physical change in the user based on the acquired ketone concentration measurement and the physical data, and outputting an evaluation result.

A physical change evaluation program of a ninth aspect of the invention causes a computer to execute processing, the processing including acquiring a ketone concentration measurement measuring ketone excreted from a user, acquiring physical data relating to the body of the user, evaluating physical change in the user based on the acquired ketone concentration measurement and the physical data, and outputting an evaluation result.

Advantageous Effects of Invention

The present invention exhibits advantageous effects of enabling easy evaluation of physical change from the past to the present, and easy evaluation of physical change from the present into the future

BRIEF DESCRIPTION OF DRAWINGS

FIG. 8 is a drawing illustrating an example of a data table showing correspondence relationships between evaluation Nos., body fat change directions, and advice information.

FIG. 9 is a drawing illustrating an example of a data table showing correspondence relationships between evaluation Nos. and advice information.

DESCRIPTION OF EMBODIMENTS

Explanation follows regarding an exemplary embodiment of the present invention.

Figure 1:
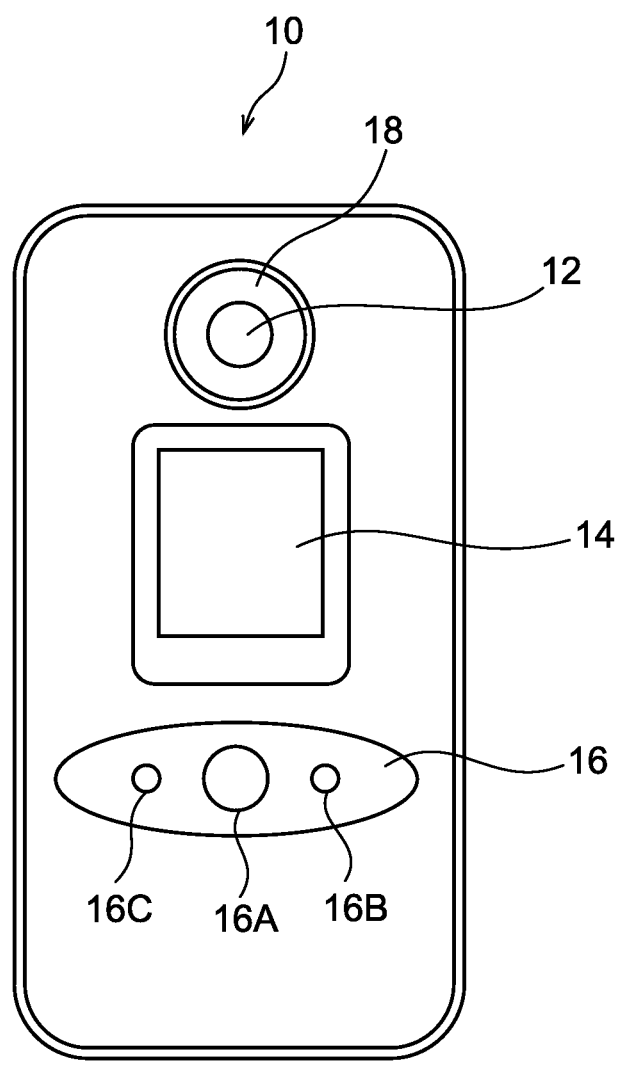
FIG. 1 is a diagram of the external appearance of a physical change evaluation device.

FIG. 1 is a diagram of the external appearance of a physical change evaluation device 10 according to the present exemplary embodiment. As illustrated in FIG. 1, the physical change evaluation device 10 includes a measurement section 12, a display section 14, and an operation section 16. The physical change evaluation device 10 according to the present exemplary embodiment is, as an example, a portable device that is convenient to be carried around.

The measurement section 12 measures the concentration of ketone excreted from a user (referred to below as ketone concentration). Ketone is a collective name employed for acetoacetic acid, 3-hydroxy acetic acid (β-hydroxy acetic acid), and acetone, and represents at least one thereof.

In the present exemplary embodiment, explanation is given of a case in which the measurement section 12 is, as an example, configured with an acetone detection sensor that detects acetone in the breath of a user. The user is able to measure the acetone concentration of exhaled breath by blowing air into a blow-in hole 18. In order to facilitate collection of exhaled air, the blow-in hole 18 may be a mouthpiece typed shaped so as to be capable of being held in the mouth, or may be a mask type shaped as a mask.

The display section 14 is configured, for example, by a liquid crystal panel or the like. Various screen images are displayed on the display section 14, such as various setting screen images, the measurement results of acetone concentration measured by the measurement section 12, and advice information based on the measured acetone concentration. The display section 14 may also be configured including a touch panel function, and may be configured to enable operation by directly touching the screen image.

The operation section 16 is configured including plural operation buttons, and FIG. 1 illustrates an example of a case in which there are 3 individual operation buttons 16A to 16C provided.

The operation button 16A functions, as an example, as a button to operate to switch the power source of the physical change evaluation device 10 ON/OFF, and to make selections on various screen images.

The operation button 16B functions, as an example, as a button to input data on various screen images.

The operation button 16C functions, as an example, as a button to instruct reading of past measurement results and the like.

Figure 2:
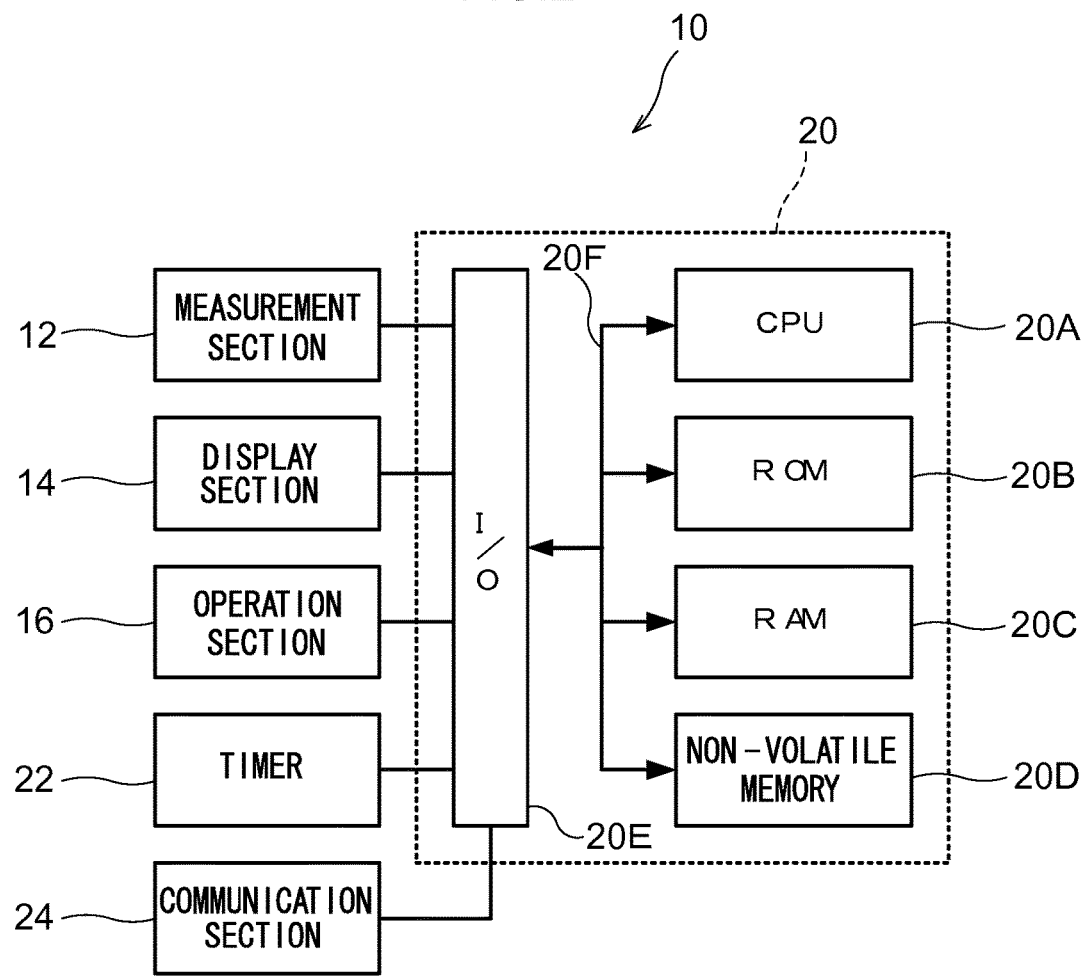
FIG. 2 is a block diagram of a physical change evaluation device.

FIG. 2 is a block diagram of the physical change evaluation device 10. As illustrated in FIG. 2, the physical change evaluation device 10 includes a controller 20. The controller 20 is configured including a Central Processing Unit (CPU) 20A, Read Only Memory (ROM) 20B, Random Access Memory (RAM) 20C, non-volatile memory 20D, and an input-output (I/O) interface 20E, each connected together through a bus 20F. In this case, a physical change evaluation program that causes the CPU 20A of the controller 20 to execute physical change evaluation processing, explained later, is, for example, pre-written to the non-volatile memory 20D, and read into and executed by the CPU 20A. The physical change evaluation program may be provided on a recording medium, such as a CD-ROM, memory card, or the like, or may be downloaded from a server, not illustrated in the drawings.

The measurement section 12, the display section 14, the operation section 16, a timer 22, and a communication section 24 are connected to the I/O interface 20E.

The timer 22 includes a function to acquire the current time, and a timing function to time a set duration.

Figure 3:
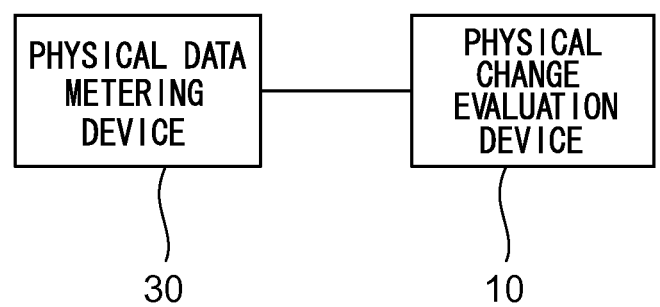
FIG. 3 is a connection diagram showing connection between a physical change evaluation device and a physical data metering device.

The communication section 24 performs transmission and reception of data to and from an external device by wireless or wired communication. As illustrated in FIG. 3, explanation is given in the present exemplary embodiment regarding a case in which a physical data metering device 30 is connected to the physical change evaluation device 10 either wirelessly, or through a cable. The physical change evaluation device 10 and the physical data metering device 30 may also be configured as an integrated device.

The physical data metering device 30 includes a function to meter physical data of the user. Physical data includes, for example, at least one out of body weight data and body composition data. Body composition data includes at least one data item relating to body composition out of, for example, body fat, subcutaneous fat, and muscle mass; but the body composition data is not limited thereto.

The physical change evaluation device 10 is capable of acquiring physical data of the user from the physical data metering device 30 through the communication section 24.

Figure 4:
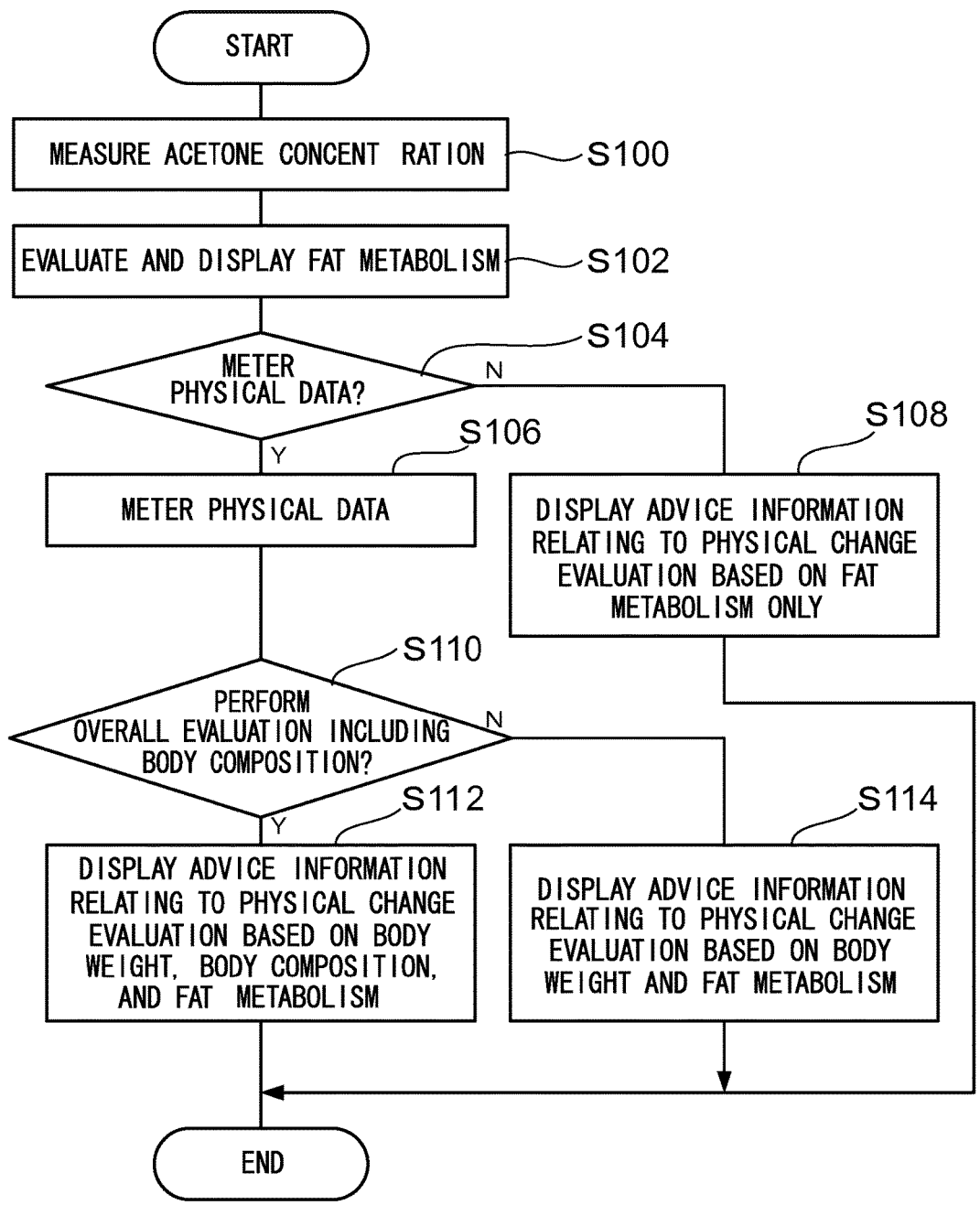
FIG. 4 is a flowchart of processing by a physical change evaluation program.

Explanation next follows, as operation of the present exemplary embodiment, regarding processing by the physical change evaluation program executed by the CPU 20A of the controller 20, with reference to the flowchart illustrated in FIG. 4. The processing in FIG. 4 is executed when a user operates the operation section 16 of the physical change evaluation device 10, and instructs execution of the physical change evaluation program.

At step S100, acetone concentration is measured. More specifically, first a message to start measuring acetone concentration is displayed on the display section 14 after a predetermined time (for example 10 seconds) has elapsed, and the timer 22 is instructed to time a predetermined duration.

Then, when notified by the timer 22 that the predetermined duration has elapsed, a blow-in start message instructing air to be exhaled through the blow-in hole 18 is displayed on the display section 14, and the measurement section 12 is instructed to start measuring the acetone concentration. The user exhales air into the blow-in hole 18 when the blow-in start message is displayed on the display section 14.

The measurement section 12 measures the acetone concentration of the air exhaled into the blow-in hole 18 and outputs the measurement to the controller 20. The measured acetone concentration is stored in the non-volatile memory 20D together with the current date and time acquired from the timer 22.

At step S102, fat metabolism is evaluated based on the acetone concentration measured at step S100, and the evaluation result is displayed on the display section 14.

The acetone concentration of acetone that is a byproduct of fat metabolism may be thought of as corresponding to the fat burn amount. The acetone concentration is lower when there is surplus sugar energy present in the body since fat is not being burnt, and the acetone concentration is higher when there is not enough sugar energy present in the body as fat is being burnt. Normally, acetone concentration starts to fall when a meal is consumed and there is excess sugar energy present in the body, after which the acetone concentration rises when there is no longer enough sugar energy in the body. Namely, fat metabolism may be said to be higher the higher the acetone concentration.

Figure 5:
FIG. 5 is a drawing illustrating an example of a data table showing correspondence relationships between acetone concentration and fat metabolism.

The fat metabolism evaluation is performed using a data table 40 such as the example illustrated in FIG. 5, showing correspondence relationships between acetone concentration and fat metabolism. The data table 40 in FIG. 5 is, for example, stored in advance in the non-volatile memory 20D. The fat metabolism evaluation may be by a simple comparison against acetone concentration, such as in the data table 40 illustrated in FIG. 5, or may be evaluation using a data table 40 adjusted by considering at least one out of the build or age of the user. Moreover, rather than using a current acetone concentration, relative evaluation may be performed as to whether the acetone concentration is rising or falling by comparison to past acetone concentration measurement results.

At step S102, the fat metabolism corresponding to the acetone concentration measured at step S100 is retrieved from the data table 40 of FIG. 5, and displayed on the display section 14. FIG. 5 illustrates a case in which, there are four levels of fat metabolism: "low", "standard", "high", and "too high". However, configuration may be made with three levels or fewer, or with five levels or more.

At step S104, determination is made as to whether or not to meter physical data. For example, a selection screen image for choosing whether or not to meter physical data and evaluate physical change is displayed on the display section 14, and the user selects whether or not to meter physical data and evaluate physical change.

Processing transitions to step S106 when the user selects to meter physical data and evaluate physical change, and processing transitions to step S108 when the user selects to evaluate physical change without metering physical data.

At step S106, physical data is acquired from the physical data metering device 30. Specifically, first, an instruction screen image instructing user physical data metering is displayed on the display section 14, instructing the user to acquire physical data using the physical data metering device 30. The user thereupon meters physical data using the physical data metering device 30. The physical data metering device 30 transmits the metered physical data to the physical change evaluation device 10. The physical change evaluation device 10 thus acquires the user's physical data. The acquired physical data is stored in the non-volatile memory 20D together with the current date and time. Note that explanation is given in the present exemplary embodiment regarding a case in which body weight and body fat are metered, and the metered data is transmitted as the physical data to the physical change evaluation device 10.

Figure 6:
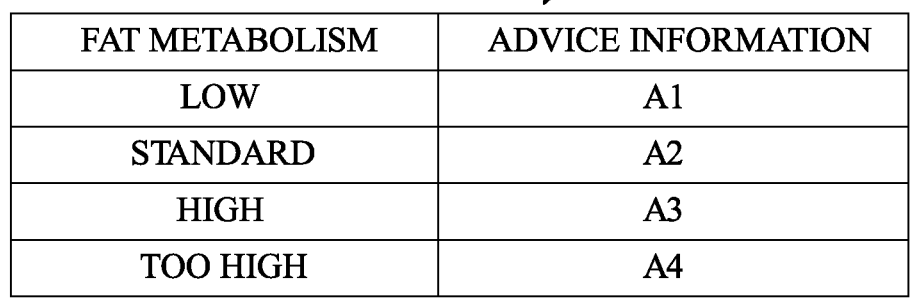
FIG. 6 is a drawing illustrating an example of a data table showing correspondence relationships between fat metabolism and advice information.

At step S108, advice information relating to the evaluation of physical change of the user based on fat metabolism alone is displayed on the display section 14. More specifically, a data table 50 showing correspondence relationships between fat metabolism and advice data relating to physical change evaluation, such as that illustrated in FIG. 6, is employed. The data table 50 illustrated in FIG. 6 is, for example, stored in advance in the non-volatile memory 20D. The advice information is information that, for example, calls for caution or offers advice regarding subsequent behavior, according to the current fat metabolism.

At step S108, advice information relating to physical change evaluation according to the fat metabolism retrieved at step S102 is retrieved from the data table 50 of FIG. 6, and displayed on the display section 14.

Measuring the acetone concentration included in the breath of the user and displaying advice relating to the physical change evaluation based on the measured acetone concentration enables the user to easily obtain a current physical change evaluation by simply measuring acetone concentration, thereby enabling the user to plan steps toward an ideal composition or ideal proportions for his or her own body.

At step S110, determination is made as to whether or not to perform overall physical change evaluation including body composition data. For example, a selection screen image for choosing whether or not to perform overall physical change evaluation including body composition data is displayed on the display section 14, and the user selects whether or not to perform overall physical change evaluation including body composition data.

Processing transitions to step S112 when the user has selected to perform overall physical change evaluation including body composition data, and processing transitions to step S114 when the user has selected not to perform overall physical change evaluation including body composition data, namely when the user selects to evaluate physical change using only body weight data.

At step S112, advice information relating to the physical change evaluation based on the body weight data, body composition data, and the fat metabolism is displayed on the display section 14. More specifically, first body weight measured in the past is read from the non-volatile memory 20D, and a difference between the read past body weight and the current body weight, namely a body weight change Δ (kg) is derived as a comparison result. The past body weight read from the non-volatile memory 20D may be the body weight measured the previous time, or may be the body date of the previous day, or may be the body weight one week earlier, and how far in the past to read the body weight may be set in advance. In the present exemplary embodiment, the difference is derived as the comparison result between the past body weight and the current body weight, but there is no limitation to using the difference to express the comparison result. For example, a change ratio may be derived between the past body weight and the current body weight.

Figure 7:
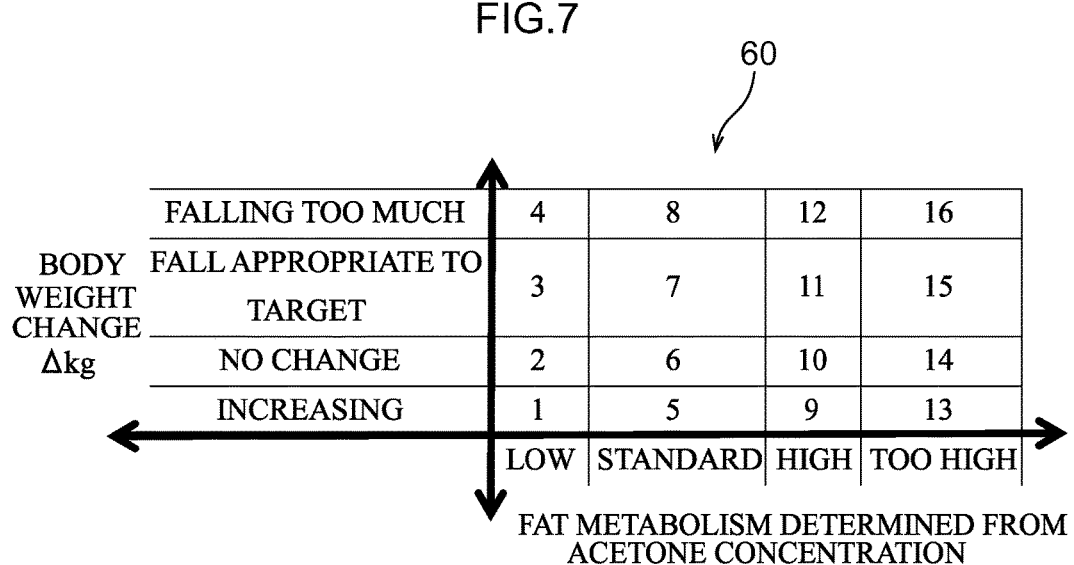
FIG. 7 is a drawing illustrating an example of a data table showing correspondence relationships between fat metabolism, body weight change, and evaluation Nos.

Then, an evaluation No. corresponding to the fat metabolism retrieved at step S102 and the body weight change Δ calculated at step S112 is derived based on a data table 60 showing correspondence relationships between fat metabolism, body weight change, and the evaluation No., such as that illustrated in FIG. 7. In the example illustrated in FIG. 7, the body weight change Δ is divided into four change levels: "falling too much", "fall appropriate to target", "no change", and "increasing". Body weight change Δ ranges for each change level are set in advance, and the evaluation No. is derived based on the change level corresponding to the derived body weight change Δ, and the fat metabolism retrieved at step S102. In the example illustrated in FIG. 7, the fat metabolism and the body weight change Δ are each categorized into four levels, such that the respective evaluation Nos. can take the values 1 to 16.

Next, based on the derived evaluation No. and the body fat acquired at step S106, advice information relating to the physical change evaluation is acquired and displayed on the display section 14. More specifically, first, body fat measured in the past is read from the non-volatile memory 20D, and the read past body fat is compared against the current body fat to determine whether or not the direction of body fat change is an upward direction or a downward direction. The past body fat read from the non-volatile memory 20D may be the body fat measured the previous time, or may be the body fat of the previous day, or may be the body fat of one week earlier, and how far in the past to read the body fat may be set in advance.

Next, advice information corresponding to the evaluation No. derived at the present step and the body fat change direction is acquired based on a data table 70 such as that illustrated in FIG. 8, and displayed on the display section 14. In FIG. 8, "body fat UP" indicates that the body fat change direction is an upward direction, and "body fat DOWN" indicates that the body fat change direction is a downward direction. If the past body fat and the current body fat are the same as each other, the body fat change direction may be classed as an upward direction or classed as a downward direction, and may be included in a predetermined change direction.

The acetone concentration included in the breath of the user, body weight, and body fat are thereby measured, overall physical change evaluation is performed based on the measurement results thereof, and advice information relating to the overall evaluation is displayed. This thereby enables the user to easily obtain physical change evaluation regarding the past, the present, and the future, thereby enabling the user to plan steps toward an ideal composition or ideal proportions for his or her own body.

At step S114, advice information relating to the physical change evaluation based on the body weight data and the fat metabolism is displayed on the display section 14. More specifically, first, similarly to at step S112, the body weight change Δ (kg) is derived, and the evaluation No. is derived corresponding to the fat metabolism retrieved at step S102 and the body weight change Δ calculated in at step 114 based on the data table 60 illustrated in FIG. 7.

Next, advice information relating to the physical change evaluation corresponding to the evaluation No. derived in the present step is acquired based on a data table 80 such as that illustrated in FIG. 9, showing correspondence relationships between the evaluation Nos. and the advice information relating to the physical change evaluation, and is displayed on the display section 14.

The acetone concentration included in the breath of the user and body weight are thereby measured, and advice information relating to the physical change evaluation based on the measurement results is displayed. This thereby enables the user to easily obtain physical change evaluation regarding the past, the present, and the future, thereby enabling the user to plan steps toward an ideal composition or ideal proportions for his or her own body.

In the present exemplary embodiment, explanation has been given regarding a case in which the body weight change Δ is plotted on the vertical axis of the data table 60 of FIG. 7, but the vertical axis may be configured by other change amounts for body composition data, such as a body fat Δ (mm), or a subcutaneous fat Δ (mm).

In the present exemplary embodiment, the body fat change direction is employed in the data table 60 of FIG. 8, but the body weight change direction may be employed, or another body composition change direction may be employed, such as for subcutaneous fat.

Namely, the body weight data and the body composition data employed in physical change evaluation may be combined as appropriate.

In the present exemplary embodiment, explanation has been given regarding a case in which the physical data metering device 30 is connected to the physical change evaluation device 10, and physical data of the user is acquired from the physical data metering device 30. However, configuration may be made in which the physical data metering device 30 is not connected to the physical change evaluation device 10, and physical data metered by the physical data metering device 30 is input directly by the user operating the operation section 16 of the physical change evaluation device 10.

Figure 10:
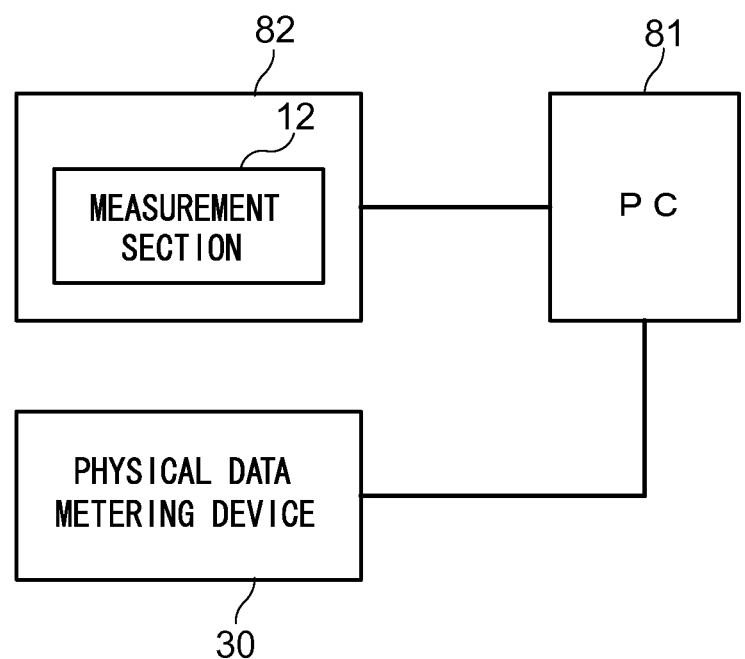
FIG. 10 is a block diagram illustrating a connection between a measurement instrument and a personal computer.

Although explanation has been given in the present exemplary embodiment regarding a case in which the physical change evaluation device 10 is a dedicated portable device, configuration may be made in which a measurement instrument 82 including a measurement section 12 and the physical data metering device 30 are connected by wire, or wirelessly, to a personal computer 81, as illustrated in FIG. 10. In such cases the personal computer 81 functions as a physical change evaluation device by acquiring an acetone concentration measured by the measurement instrument 82, acquiring the physical data metered by the physical data metering device 30, and executing the processing illustrated in FIG. 4.

The device connected to the measurement instrument 82 and the physical data metering device 30 is not limited to a personal computer, and may be a portable terminal such as a mobile phone, a smart phone, or a tablet terminal. The measurement section 12 may also be built into such a portable terminal. Configuration may be made such that a portable terminal or the measurement instrument 82 and the physical data metering device 30 are connected to a server over a network. In such cases the server functions as the physical change evaluation device. Namely, the portable terminal or the measurement instrument 82 transmits the measured acetone concentration and the physical data to a server, and the physical data metering device 30 transmits the metered physical data to the server. The server then executes the processing illustrated in FIG. 4 based on the acetone concentration received from the portable terminal or the measurement instrument 82 and the physical data received from the physical data metering device 30, and transmits the result to the portable terminal or the measurement instrument 82. The measurement instrument 82 may thereby be provided with minimum functionality of measuring and transmitting the acetone concentration to the server, and functionality to receive the result from the server and display, enabling a cost effective configuration to be achieved.

Explanation has been given in the present exemplary embodiment regarding a case in which the measurement section 12 is configured including an acetone detection sensor that detects acetone on the breath, but there is no limitation thereto, and configuration may be made in which a ketone detection sensor is provided that detects excreted ketone, such as in the skin, urine, saliva, or sweat of a user.

What is claimed is:

1. A physical change evaluation device comprising:
    a ketone concentration sensor configured to acquire a ketone concentration measurement measuring ketone excreted from a user;
    a physical data meter configured to acquire body weight data of the user and body fat data of the user;
    a storage unit configured to store body weight data of the user and body fat data of the user, wherein the storage unit has stored a three-dimensional lookup table containing entries based on the variables (1) ketone concentration, (2) body weight change, and (3) body fat change direction;

a processor configured to (i) determine a body weight change by comparing current body weight data of the user with past body weight data of the user that is stored in the storage unit, (ii) determine a body fat change direction by comparing current body fat data of the user with past body fat data of the user that is stored in the storage, and (iii) retrieve from the three-dimensional lookup table the respective entry associated with the ketone concentration measurement acquired by the ketone concentration sensor, the calculated body weight change, and the calculated body fat change direction; and a display configured to output an evaluation result by the processor.

2. The physical change evaluation device of claim 1, wherein the display is configured to output advice information corresponding to the evaluation result.

3. The physical change evaluation device of claim 1, wherein the ketone excreted from the user are acetone contained in breath exhaled from the user.

4. A physical change evaluation method comprising:
acquiring a ketone concentration measurement measuring ketone excreted from a user;
acquiring body weight data of the user and body fat data of the user at a first time;
storing the body weight data of the user and the body fata data of the user at the first time;
acquiring body weight data of the user and body fat data of the user at a second time;
determining a body weight change by comparing the body weight data of the user at the second time with body weight data of the user at the first time;
determine a body fat change direction by comparing body fat data of the user at the second time with body fat data of the user at the first time;
retrieving from a three-dimensional lookup table the respective entry associated with the acquired ketone concentration measurement, the calculated body weight change, and the calculated body fat; and
outputting an evaluation result.

5. A non-transitory recording medium stored with a physical change evaluation program that causes processing to be executed on a computer, the processing comprising:
acquiring a ketone concentration measurement measuring ketone excreted from a user;
acquiring body weight data of the user and body fat data of the user at a first time;
storing the body weight data of the user and the body fata data of the user at the first time;
acquiring body weight data of the user and body fat data of the user at a second time;
determining a body weight change by comparing the body weight data of the user at the second time with body weight data of the user at the first time;
determine a body fat change direction by comparing body fat data of the user at the second time with body fat data of the user at the first time;
retrieving from a three-dimensional lookup table the respective entry associated with the acquired ketone concentration measurement, the calculated body weight change, and the calculated body fat; and
outputting an evaluation result.

6. The physical change evaluation device of claim 1, wherein:
the processor is configured to evaluate fat metabolism based on the ketone concentration measurement;
the processor is further configured to (i) permit a user to select an evaluation without measuring the physical data, (ii) when a user selects an evaluation without measuring the physical data, retrieve an entry from a lookup table containing entries based on the measured fat metabolism and generate advice information on the retrieved entry, and (iii) transmit the advice information to the display;
the processor is further configured to (i) permit a user to select an evaluation based on fat metabolism, body weight change, and body fat change direction, (ii) when a user selects an evaluation based on fat metabolism, body weight change, and body fat change direction, retrieve from the three-dimensional lookup table the respective entry based on the measured fat metabolism, the calculated body weight change, and the calculated body fat change direction and generate advice information on the retrieved entry, and (iii) transmit the advice information to the display; and
the processor is further configured to (i) permit a user to select an evaluation based on fat metabolism and body weight change, (ii) when a user selects an evaluation based on fat metabolism and body weight change, retrieve from a two-dimensional lookup table the respective entry based on the measured fat metabolism and the calculated body weight change and generate advice information on the retrieved entry, and (iii) transmit the advice information to the display.

* * * * *